United States Patent
Zhou et al.

(10) Patent No.: US 12,369,832 B2
(45) Date of Patent: Jul. 29, 2025

(54) CLINICAL CONTEXTUAL ELECTROCARDIOGRAM MONITORING

(71) Applicant: KONINKLIJKE PHILIPS N.V., Eindhoven (NL)

(72) Inventors: Sophia Huai Zhou, Cambridge, MA (US); Richard Earl Gregg, Cambridge, MA (US)

(73) Assignee: Koninklijke Philips N.V., Eindhoven (NL)

( * ) Notice: Subject to any disclaimer, the term of this patent is extended or adjusted under 35 U.S.C. 154(b) by 562 days.

(21) Appl. No.: 17/625,352

(22) PCT Filed: Jul. 8, 2020

(86) PCT No.: PCT/EP2020/069272
§ 371 (c)(1),
(2) Date: Jan. 7, 2022

(87) PCT Pub. No.: WO2021/005119
PCT Pub. Date: Jan. 14, 2021

(65) Prior Publication Data
US 2022/0265196 A1 Aug. 25, 2022

Related U.S. Application Data

(60) Provisional application No. 62/871,738, filed on Jul. 9, 2019.

(51) Int. Cl.
*A61B 5/333* (2021.01)
*A61B 5/339* (2021.01)
(Continued)

(52) U.S. Cl.
CPC .............. *A61B 5/333* (2021.01); *A61B 5/339* (2021.01); *G11B 27/10* (2013.01); *G16H 40/40* (2018.01);
(Continued)

(58) Field of Classification Search
CPC ....... A61B 5/0006; A61B 5/318; A61B 5/333; A61B 5/339; A61B 5/346; A61B 5/349;
(Continued)

(56) References Cited

U.S. PATENT DOCUMENTS 5,619,995 A 4/1997 Lobodzinski
6,375,614 B1 4/2002 Braun
(Continued)

FOREIGN PATENT DOCUMENTS

JP H06154213 A 6/1994

OTHER PUBLICATIONS

Shihabuddin, B. et al., "The value of combined ambulatory cassette-EEC and video monitoring in the differential diagnosis of intractable seizures". Clinical Neurophysiology, Elsevier, Amsterdam, NL, vol. 110, No. 8, (May 24, 2017), pp. 1452-1457.
(Continued)

*Primary Examiner* — Scott Luan

(57) ABSTRACT

Various embodiments of the present disclosure encompass an ECG control network of ECG test controller (10) and ECG context controller (40). The ECG test controller (10) control a recording of an ECG test. The ECG context controller (40) control a synchronization of the recording of the ECG test by the ECG test controller (10) with a recording of a video clip illustrative of a clinical context of the ECG test and/or a recording of an audio clip informative of a clinical context of the ECG test. The ECG context controller (40) further control a simultaneous presentation of a display of the recording of the ECG test with of a playing of the video clip contextually interpretative of the ECG test and/or a playing of the audio clip contextually interpretative of the ECG test.

20 Claims, 11 Drawing Sheets

(51) Int. Cl.
  *G11B 27/10* (2006.01)
  *G16H 40/40* (2018.01)
  *G16H 40/67* (2018.01)
  *G16H 50/20* (2018.01)
  *H04N 5/765* (2006.01)
  *H04N 5/92* (2006.01)

(52) U.S. Cl.
  CPC ............. *G16H 40/67* (2018.01); *G16H 50/20* (2018.01); *H04N 5/765* (2013.01); *H04N 5/9202* (2013.01)

(58) Field of Classification Search
  CPC .... A61B 5/6833; A61B 5/743; A61N 1/3904; G11B 27/10; G16H 40/40; G16H 40/63; G16H 40/67; G16H 50/20; H04N 5/765; H04N 5/9202
  See application file for complete search history.

(56) References Cited

U.S. PATENT DOCUMENTS

| | | | |
|---|---|---|---|
| 2002/0052559 A1 | 5/2002 | Watrous | |
| 2008/0009752 A1 | 1/2008 | Butler | |
| 2012/0295589 A1* | 11/2012 | Alexander | H04L 63/0861 455/414.1 |
| 2015/0313502 A1 | 11/2015 | Mestha | |
| 2018/0092574 A1 | 4/2018 | Tzvieli | |
| 2019/0198059 A1 | 6/2019 | Baier | |

OTHER PUBLICATIONS

Shihabuddin, B. et al., "The value of combined ambulatory cassette-EEC and vido monitoring in the differential diagnosis of intractable seizures". Clinical Neurophsiology, Amsterdam, NL, vol. 110, No. 8, (May 24, 2017), pp. 452-1457.

Edmondstone, W.M. "Cardiac chest pain: does body language help the diagnosis?". BMJ. 1995; 311: p. 23-30.

Kligfield, P. et al. Recommendations for the Standardization and Interpretation of the Electrocardiogram: Part I: The Electrocardiogram and Its Technology.: JACC. 2007; 49(10): p. 1109-1127.

Mason, J.W. et al., "Recommendations for the Standardization and Interpretation of the Electrocardiogram: Part II: Electrocardiogramagnostic Statement List." JACC. 2009; 49(10): p. 1128-1135.

Surawicz, B. et al., SuAHA/ACCF/HRS recommendations for the standardizaion and interpretation of the electrocardiogram: part III: intraventricular conduction disturbances.: JACC. 2009; 53(11): p. 976-81.

Rautaharju, P. et al., "AHA/ACCF/HRS Recommendations for the Standardization and Interpretation of the Electrocardiogram: Part IV: The ST Segment, T and U Waves, and the QT Interval." JACC. 2009; 53(11).

Hancock, E.W. et al., AHA/ACCF/HRS Recommendations for the Standardization and Interpretation of the Electrocardiogram: Part V: Electrocardiogram Changes Associated with Cardiac Chamber Hypertrophy. JACC. 2009; 53(11): p. 992-1002.

Wagner, G.S. et al., "AHA/ACCF/HRS Recommendations for the Standardization and Interpretation of the Electrocardiogram. Part VI: Acute Ischemia/Infraction." Circulation. 2009; 119: p. e1-9.

Thygesen, K. et al., "Third Universal Definition of Myocardial Infraction." Circulation. 2012; 126: p. 2020-2035.

Gregg, R. et al., What is inside the electrocardiogramactrocardiology 41 (2008) 8-14.

Zhou, S. et al., "New approach in Philips ECG database management system design." IEEE Computing in Cardiology processing, 2003;30:267-270.

International Search Report for PCT/EP2020/069272 filed Jul. 8, 2020.

* cited by examiner

CLINICAL CONTEXTUAL ELECTROCARDIOGRAM MONITORING

This application is a national stage application under 35 U.S.C. § 371 of International Application No. PCT/EP2020/069272 filed on Jul. 8, 2020 and published in the English language on Jan. 14, 2021 as International Publication No. WO2021/005119, which claims priority to U.S. Patent Application No. 62/871,738 filed on Jul. 9, 2019, the entire disclosures of which are incorporated herein by reference.

FIELD OF THE INVENTION

The present disclosure generally relates to electrocardiograph procedures for measuring an electrical activity of a heart. The present disclosure specifically relates to an electrocardiogram monitoring of the electrical activity of a heart within a relevant clinical context.

BACKGROUND OF THE INVENTION

Electrocardiograph (ECG) is a mature cardiology diagnostic tool, and has been widely used in clinics and hospitals within all countries. As a cardiology diagnostic tool, an ECG test may be performed for a variety of different purposes including, but not limited to, annual health check-ups, pre-surgical screening, and diagnosing a variety of cardiac conditions ranging from arrhythmias (e.g., atrial fibrillation, ventricular tachycardia, second degree AV block, third degree AV block, etc.) to morphology abnormalities (e.g., left ventricular hypertrophy, acute cardiac ischemia, acute myocardial infarct, etc.). Importantly, ECG technology is proven and ECG criteria for reading and interpreting (i.e., diagnosing) ECG reports are well established.

However, ECG diagnoses experiences similar limitations as imaging diagnoses. For example, an ECG diagnosis involves a degree of reading and interpretation that requires a high level of expertise (e.g., trained cardiologists), and therefore a reading and an interpretation of an ECG test of a patient by an expert is normally not done in real-time within a clinical context of the patient.

For example, an ECG of a patient is usually recorded by an ECG technician in a clinic or at a patient room in a hospital, and the recorded ECG is subsequently transferred to a cardiology department or an emergency department whereby a cardiologist on duty is able to comprehensively read and interpret the ECG recording without the distractions of a clinic or patient room. However, the transfer of the recorded ECG adds a delay between the ECG recording and the ECG reading/interpretation, which sometimes may be a significant delay depending upon the circumstances of the patient. Consequently, the cardiologist would not have an opportunity to see the patient in real-time, and would thus unaware of the patient's symptoms at the time of the ECG recording.

By further example, a patient visiting a clinic with chest pain or shortness of breath may be suspected of having acute cardiac ischemia (ACI) or acute myocardial infarct (AMI). As such, a common sign on the recorded ECG of the patient is ST-segment elevation, ST-segment depression, or inverted T on some leads. Without seeing the patient in real-time or being aware of the patient symptoms of chest pain, sweating, or shortness of breath, the cardiologist may diagnosis the ECG tests as indicating ACI or AMI when the ECG changes (e.g., ST-segment elevation, ST-segment depression, or inverted T wave) could be due in fact to a chronic condition (e.g., left ventricular hypertrophy) or a benign condition (e.g., early repolarization).

SUMMARY OF THE INVENTION

The present disclosure describes a novel, unique clinical contextual ECG recording and diagnosis that will help cardiologists improve upon reading and interpreting ECG test recordings with higher accuracy, confidence in their ECG diagnosis, and reduced time to look for previous ECGs for serial comparison.

The present disclosure may be embodied as:
(1) an ECG control network employing an ECG test controller and an ECG context controller controlling a recording and a display of ECG tests within a relevant clinical context;
(2) an ECG context controller including an ECG context recording subcontroller controlling a recording of ECG tests in a relevant clinical context, and an ECG context reading subcontroller controlling a display of ECG tests within a relevant clinical context;
(3) an ECG control method utilizing the ECG control network for controlling a recording and a display of ECG tests within a relevant clinical context; and
(4) an ECG context testing and diagnostic device including an ECG test controller and an ECG context controller controlling a recording and a display of ECG tests within a relevant clinical context established by a video source and/or an audio source.

Various ECG control network embodiments of the present disclosure encompass an ECG test controller installed within an ECG monitor device or an ECG therapy device for controlling a recording an ECG test.

Various ECG control network embodiments of the present disclosure further encompass an ECG context controller installed within the ECG monitor device, the ECG therapy device, an ECG workstation and/or an ECG server for controlling a synchronization of the recording of the ECG test by the ECG test controller with a recording of a video clip illustrative of a clinical context of the ECG test and/or a recording of an audio clip informative of the clinical context of the ECG test, and for further controlling a simultaneous presentation of the display of the recording of the ECG test with a playing of the video clip and/or a playing of the audio clip.

Various ECG context controller embodiments encompass an ECG context recording subcontroller installed within an ECG monitor device, an ECG therapy device or an ECG workstation for controlling a synchronization of a recording of an ECG test with a recording of a video clip illustrative of a clinical context of the ECG test and/or a recording of an audio clip informative of a clinical context of the ECG test.

Various ECG context controller embodiments further encompass an ECG context diagnostic subcontroller installed within the ECG monitor device, the ECG therapy device, the ECG workstation or an ECG server for controlling a simultaneous presentation of the display of the recording of the ECG test with a playing of the video clip and/or a playing of the audio clip.

Various ECG control method embodiments of the present disclosure encompass controlling, via an ECG test controller, a recording of an ECG test.

Various ECG context testing and diagnostic method embodiments of the present disclosure further encompass controlling, via an ECG context controller, a synchronization of the recording of the ECG test by the ECG test controller with at a recording of a video clip illustrative of a clinical context of the ECG test and/or a recording of an audio clip informative of a clinical context of the ECG test, and controlling, via the ECG context controller, a simultaneous presentation of the display of the recording of the ECG test by the ECG test controller with a playing of the video clip and/or a playing of the audio clip.

Various context testing and diagnostic device embodiments encompass an ECG test controller and an ECG context controller installed within an ECG monitoring device or an ECG therapy device for controlling a recording and a display of ECG tests within a relevant clinical context established by a video source and/or an audio source. If included, the video source is in communication with the ECG context controller and may be installed within, externally coupled to or pluggable into to the ECG monitoring device or the ECG therapy device. If included, the audio source is in communication with the ECG context controller and may be installed within, externally coupled to or pluggable into to the ECG monitoring device or the ECG therapy device.

For purposes of the description and claims of the present disclosure:

(1) terms of the art including, but not limited to, "ECG test", "network", "ECG monitoring device", "ECG therapy device", "ECG workstation", "ECG server", "recording (and tenses thereof)", "synchronization (and tenses thereof)", "presentation (and tenses thereof)", "playing (and tenses thereof)", "displaying (and tenses thereof)", "video source", "video clip", "audio source", and "audio clip" are to be interpreted as known in the art of the present disclosure and as exemplary described in the present disclosure;

(2) the phrase "illustrative of the clinical context of the ECG test" broadly encompasses an illustration of a clinical pose, a clinical examination and/or a clinical exercise/movement of a patient as the patient is being administered the ECG test as exemplary described in the present disclosure;

(3) the phrase "informative of the clinical context of the ECG test" broadly encompasses information related to the clinical status of the patient as the patient is being administered the ECG test as exemplary described in the present disclosure;

(4) the terms "controller" and "subcontroller" broadly encompasses all structural configurations, as understood in the art of the present disclosure and as exemplary described in the present disclosure, of main circuit board or integrated circuit for controlling an application of various principles of the present disclosure for implementing an ECG related function in accordance with the present disclosure. The structural configuration of the controller may include, but is not limited to, processor(s), computer-usable/computer readable storage medium(s), an operating system, application module(s), peripheral device controller, slot(s) and port(s). A controller and a subcontroller may be housed within or communicatively linked to an ECG monitoring device, an ECG therapy device, an ECG workstation and/or an ECG server;

(5) the term "application module" broadly encompasses an application incorporated within or accessible by a controller consisting of an electronic circuit (e.g., electronic components and/or hardware) and/or an executable program (e.g., executable software stored on non-transitory computer readable medium(s) and/or firmware) for executing a specific application associated with an ECG related function in accordance with the present disclosure; and (6) the terms "signal", "data" and "command" broadly encompasses all forms of a detectable physical quantity or impulse (e.g., voltage, current, or magnetic field strength) as understood in the art of the present disclosure and as exemplary described in the present disclosure for transmitting information and/or instructions in support of applying various inventive principles of the present disclosure as subsequently described in the present disclosure. Signal/data/command communication various components of the present disclosure may involve any communication method as known in the art of the present disclosure including, but not limited to, signal/data/command transmission/reception over any type of wired or wireless datalink and a reading of signal/data/commands uploaded to a computer-usable/computer readable storage medium.

The foregoing embodiments and other embodiments of the present disclosure as well as various structures and advantages of the present disclosure will become further apparent from the following detailed description of various embodiments of the present disclosure read in conjunction with the accompanying drawings. The detailed description and drawings are merely illustrative of the present disclosure rather than limiting, the scope of the present disclosure being defined by the appended claims and equivalents thereof.

BRIEF DESCRIPTION OF THE DRAWINGS

The present disclosure will present in detail the following description of exemplary embodiments with reference to the following figures wherein.

DETAILED DESCRIPTION OF THE PREFERRED EMBODIMENTS

The present disclosure is applicable to numerous and various electrocardiograph (ECG) monitoring and therapy applications.

The present disclosure improves upon the prior art by providing a recording and a display of ECG tests within a relevant clinical context.

For example, body language of patient has proven to be an accurate predicator of a diagnosis of specific types of heart ailments/diseases. In some cases, body language of the patient has proven to be the only accurate predicator of a diagnosis of specific types of heart ailments/diseases. The presence disclosure provides for a synchronized recording of an ECG test of a patient and a video clip illustrative of the body language of the patient to thereby provide for an accurate ECG diagnosis for such heart ailments/diseases.

More particularly, in a study of clinical context in a chest pain setting, it has been shown that hand motions when describing chest pain can predict with good accuracy if a myocardial infarction will be diagnosed later by the typical extensive myocardial infarction examination. The presence disclosure provides for a synchronized recording of an ECG test of a patient and a video clip illustrative of the body language of the patient to thereby provide for an accurate prediction of myocardial infarction or any other type of heart ailments/diseases predictive from body language prior to an extensive examination of the heart ailment/disease.

Additionally, the present disclosure provides a synchronized recording of an ECG test of a patient and an audio clip informative of an explanation by the patient of his/her clinical status (e.g., symptoms, medical history related to the symptoms, etc.) that is further contributing factor to an accurate diagnosis of an ECG test.

Figure 1:
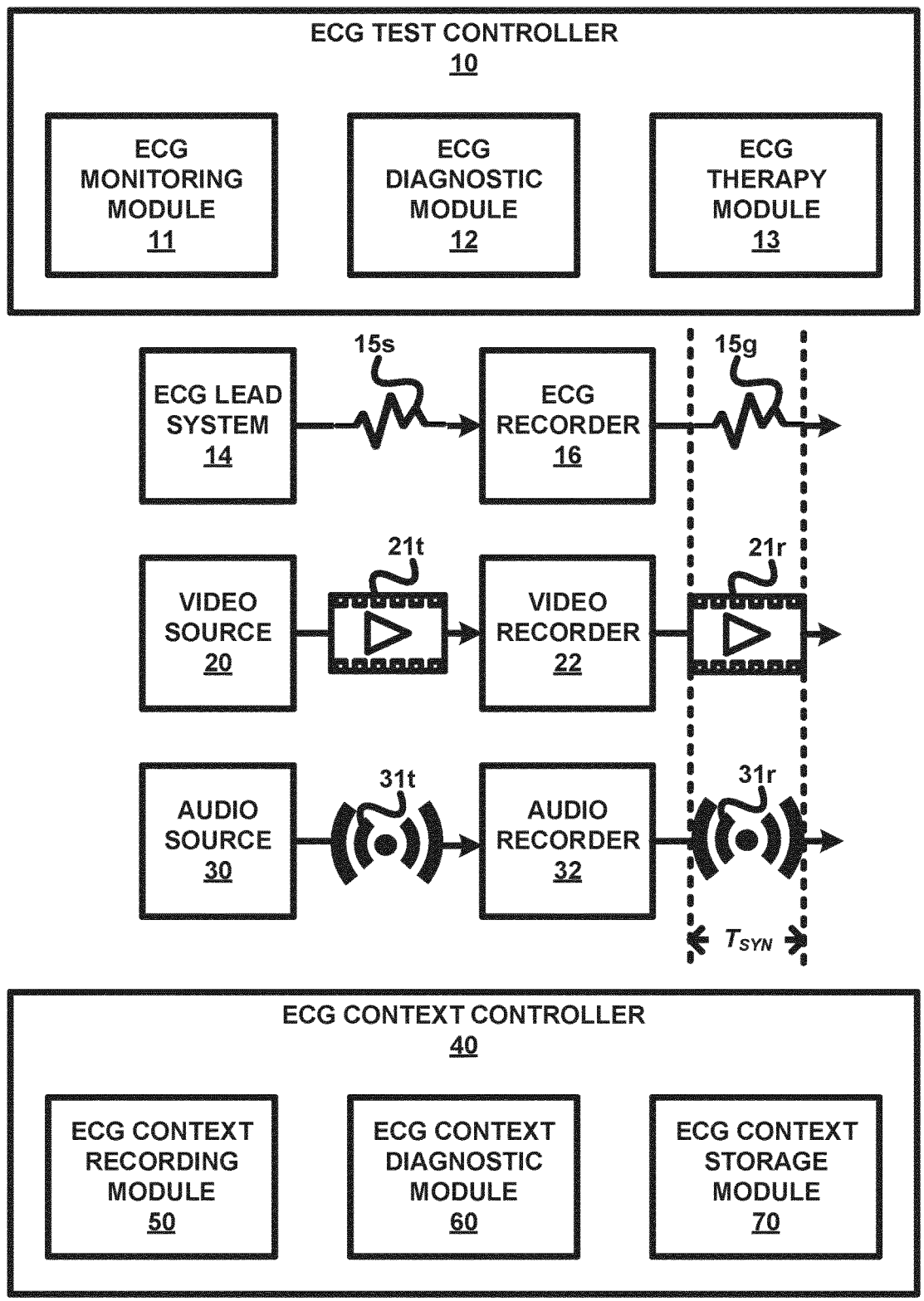
FIG. 1 illustrates an exemplary embodiment of an ECG control network in accordance with the present disclosure.

To facilitate an understanding of the present disclosure, the following description of FIG. 1 teaches exemplary embodiments of an ECG context testing and diagnosis control network in accordance with the present disclosure. From the description of FIG. 1, those having ordinary skill in the art of the present disclosure will appreciate how to apply the present disclosure to make and use additional embodiments of an ECG context testing and diagnosis control network in accordance with the present disclosure.

Referring to FIG. 1, an ECG context testing and diagnosis control network of the present disclosure employs an ECG test controller 10.

ECG test controller 10 includes a version of an ECG monitoring module 11 as known in the art of the present disclosure or hereinafter conceived for receiving ECG lead signals 15s of an electrical activity of a heart from a connection to a patient (not shown) via a version of an ECG lead system 14 as known in the art of the present disclosure or hereinafter conceived, and for recording the ECG lead signals 15s in the form of an ECG graph 15g within a version of an ECG recorder 16 as known in the art of the present disclosure or hereinafter conceived.

ECG test controller 10 may further include a version of an ECG diagnostic module 12 as known in the art of the present disclosure or hereinafter conceived for identifying heart condition(s) of a patient derived from a reading and an interpretation of the recorded ECG graph 15g. Examples of such heart conditions include, but are not limited to, an abnormal heart rate, an irregular heart rhythm, a previous or on-going heart attack, inadequate blood/oxygen supply to the heart and structural abnormalities of the heart.

ECG test controller 10 may further include a version of an ECG therapy module 13 as known in the art of the present disclosure or hereinafter conceived for applying a therapy to the patient based on the identified heart condition(s) of the patient derived from the reading and the interpretation of the recorded ECG graph 15g. Examples of such therapy include, but are not limited to, defibrillator shocking therapies and pacing therapies.

In practice, ECG test controller 10 may be installed within an ECG monitoring device, or an ECG therapy device.

Examples of ECG monitoring devices include, but are not limited to, Page Writer TC series of cardiographs, Intellivue ECG monitors and ST80i ECG stress systems, all currently commercially offered by Philips.

Examples of ECG therapy devices include, but are not limited to, HeartStart MRx monitor-defibrillators currently commercially offered by Philips.

Still referring to FIG. 1, the ECG context testing and diagnosis control network of the present disclosure further employs an ECG context controller 40.

ECG context controller 40 includes an ECG context recording module 50 for controlling a synchronization of a recording of a video clip 21r and/or a recording of an audio clip 31r with the recording of the ECG graph 15g.

In one exemplary video clip embodiment, over a synchronization time period $T_{SYN}$, ECG context recording module 50 controls a video transmission 21t from a video source 20 to a video recorder 22 in sync with the receiving of the ECG lead signals 15s by ECG recorder 16 whereby video transmission 21t from video source 20 may be recorded by video recorder 22 as a video clip 21r.

In a second exemplary video clip embodiment, over the synchronization time period $T_{SYN}$, ECG context recording module 50 controls a recording of video clip 21r by video recorder 22 from an on-going video transmission 21t from video source 20 in sync with the recording of the ECG graph 15g.

Examples of video source 20 include, but are not limited to, a digital camera, a digital camcorder, and a webcam.

In practice, video source 20 may be installed within, externally coupled to or pluggable into to an ECG monitoring device or an ECG therapy device.

In one exemplary audio clip embodiment, over the synchronization time period $T_{SYN}$, ECG context recording module 50 controls an audio transmission 31t from an audio source 30 to an audio recorder 32 in sync with the receiving of the ECG lead signals 15s by ECG recorder 16 whereby audio transmission 31t from audio source 30 may be recorded by audio recorder 32 as an audio clip 31r.

In a second exemplary audio clip embodiment, over the synchronization time period $T_{SYN}$, ECG context recording module 50 controls a recording of audio clip 31r by audio recorder 32 from an on-going audio transmission 31t from audio source 30 in sync with the recording of the ECG graph 15g.

Examples of audio source 30 include, but are not limited to, a microphone and a headset.

In practice, audio source 30 may be installed within, externally coupled to or pluggable into to an ECG monitoring device or an ECG therapy device.

Still referring to FIG. 1, in practice, when installed in the same device, ECG test controller 10 and ECG context controller 40 may be physically segregated, partially or entirely physically integrated or logically partitioned.

Further in practice, ECG recorder 16 may be a stand-alone recorder or a component of ECG test controller 10, video recorder 22 may be a stand-alone recorder or a component of ECG context controller 40, and audio recorder 32 may be a stand-alone recorder or a component of ECG context controller 40.

Further in practice, ECG recorder 16 may be logically partitioned with video recorder 22 and/or audio recorder 32 within a non-transitory storage medium.

Still referring to FIG. 1, in practice, synchronization time period $T_{SYN}$ of recorded video clip 21r and/or recorded audio clip 41r may extend in sync over an entirety of a time period of the recorded ECG graph 15g as shown. For example, the time period of the recorded ECG graph 15g and the synchronization time period $T_{SYN}$ of recorded video clip 21r and/or recorded audio clip 41r may be sixty (60) seconds.

Alternatively in practice, synchronization time period $T_{SYN}$ of recorded video clip 21r and/or recorded audio clip 41r may extend in sync over a specified segment of the time period of the recorded ECG graph 15g. For example, the time period of the recorded ECG graph 15g may be sixty (60) seconds and the synchronization time period $T_{SYN}$ of recorded video clip 21r and/or recorded audio clip 41r may extend over the first twenty (20) second segment of the recorded ECG graph 15g, the intermediate twenty (20) second segment of the recorded ECG graph 15g or the last twenty (20) second segment of the recorded ECG graph 15g.

Still referring to FIG. 1, in practice, ECG monitoring module 10 may control a display of the recording of ECG graph 15g within an embodiment of a ECG context recording window of the present disclosure as will be further described herein whereby ECG sync recording module 50 controls a playing of the recording of the video clip 21r within the ECG context recording window.

Alternatively in practice, ECG sync recording module 50 may control a display of the recording of ECG graph 15g within an embodiment of a ECG context recording window of the present disclosure as will be further described herein whereby ECG sync recording module 50 controls a playing of the recording of the video clip 21r within the ECG context recording window Still referring to FIG. 1, ECG context controller 40 includes ECG sync diagnostic module 60 of the present disclosure for controlling a simultaneous presentation of a display of the recorded ECG graph 15g with a playing of the video clip and/or a playing of the audio clip.

In one exemplary presentation embodiment, ECG diagnostic module 12 controls a display of the recorded ECG graph 15g within an embodiment of a ECG context diagnostic window of the present disclosure as will be further described herein whereby ECG sync diagnostic module 60 retrieves the recorded video clip 21r from video recorder 22 and/or the recorded audio clip 31r from audio recorder 32 to thereby play the recorded video clip 21r and/or the recorded audio clip 31r within the ECG control diagnostic window upon or subsequent an opening of the ECG context diagnostic window.

In a second exemplary presentation embodiment, ECG sync diagnostic module 60 controls a display of the recorded ECG graph 15g within an embodiment of a ECG control diagnostic window of the present disclosure as will be further described herein whereby ECG sync diagnostic module 60 retrieves the recorded video clip 21r from a storage remote from video recorder 22 and/or the recorded audio clip 31r from a storage remote from audio recorder 22 to thereby play the respective recorded video clip 21r and/or the recorded audio clip 31r within the ECG context diagnostic window upon or subsequent to the display of the recording 15g of the ECG lead signals 15s within the ECG context diagnostic window.

Still referring to FIG. 1, in practice, ECG context controller 40 may be installed within or distributed among an ECG monitoring device, an ECG therapy device, an ECG workstation and/or an ECG server.

As previously stated herein, examples of ECG monitoring devices include, but are not limited to, Page Writer TC series of cardiographs, Intellivue ECG monitors and ST80i ECG stress systems, all currently commercially offered by Philips.

As previously stated herein, examples of ECG therapy devices include, but are not limited to, HeartStart MRx monitor-defibrillators currently commercially offered by Philips.

Examples of ECG workstations include, but are not limited to, workstations of Intellispace ECG management systems and Intellispace Cardiovascular intervention systems currently commercially offered by Philips, and mobile devices (e.g., tablets and cell phones) programmed with EGC context recording module 50 and/or ECG context diagnostic module 60.

Examples of ECG servers include, but are not limited to, servers of Intellispace ECG management systems and Intellispace Cardiovascular intervention systems currently commercially offered by Philips.

For embodiments whereby EGC context recording module 50 and/or ECG context diagnostic module 60 are distributed among devices, ECG context controller 40 may further include an ECG context storage module 70 for management of a storage of a retrievable sync file remote from the recorder(s) 22, 32 whereby the sync file would consist of the recorded ECG graph 15g in sync with recorded video clip 21r and/or recorded audio clip 31r.

Figure 2:
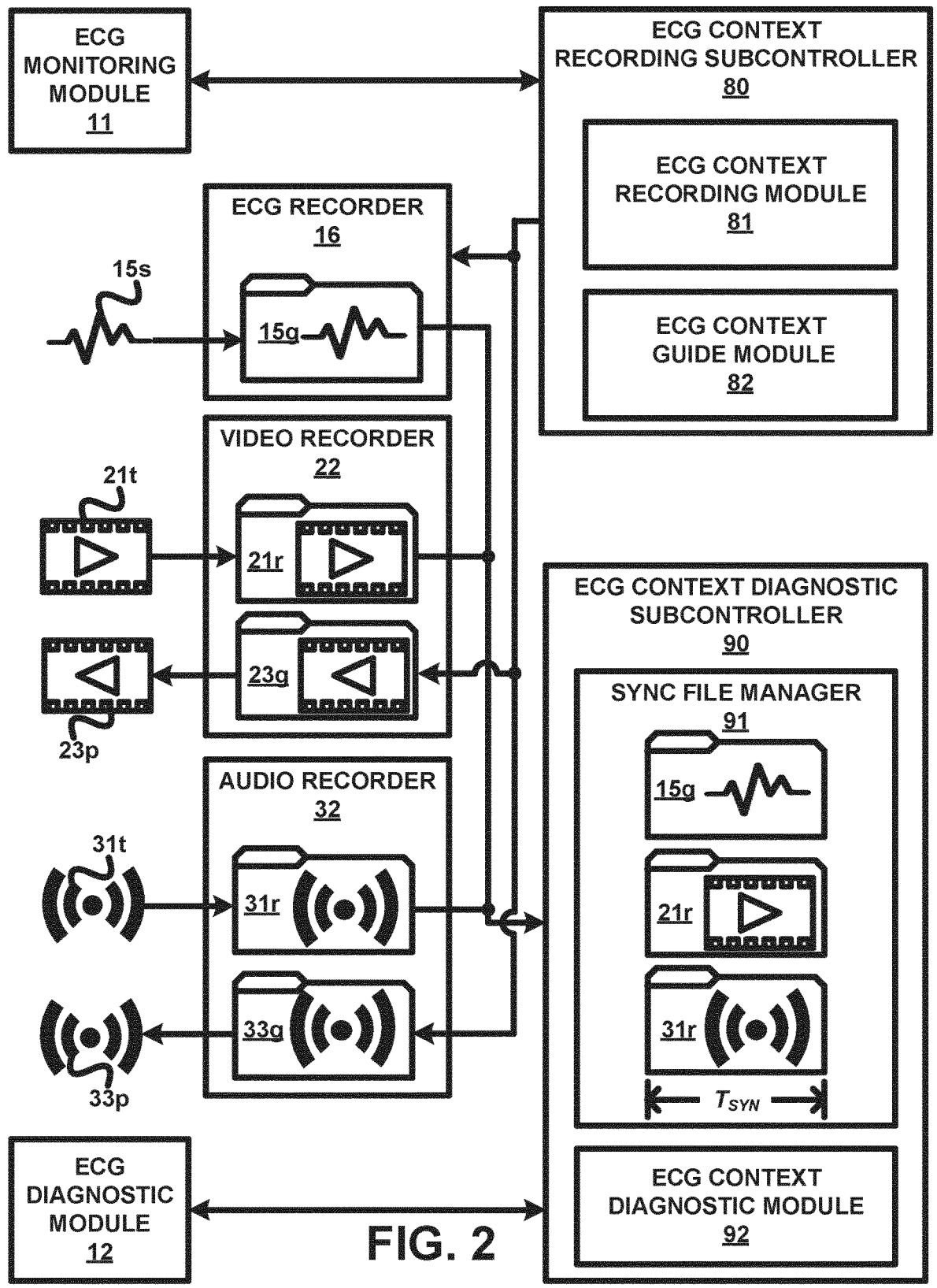
FIG. 2 illustrates an exemplary embodiment of an ECG context controller in accordance with the present disclosure.

To facilitate a further understanding of the present disclosure, the following description of FIG. 2 teaches exemplary embodiments of an ECG context controller in accordance with the present disclosure. From the description of FIG. 2, those having ordinary skill in the art of the present disclosure will appreciate how to apply the present disclosure to make and use additional embodiments of an ECG context controller in accordance with the present disclosure.

Referring to FIG. 2, an exemplary embodiment of ECG context controller 40 (FIG. 1) includes an ECG context recording subcontroller 80 and an ECG context diagnostic subcontroller 90.

In practice, ECG context recording subcontroller 80 includes ECG context recording module 81 for controlling a synchronization of a recording of EGC lead signal 15s as previously described in the present disclosure with a recording of a video transmission 21t as a video clip 21r within video recorder 22 as previously described in the present disclosure and/or with a recording of an audio transmission 31t as an audio clip 31r within audio recorder 32 as previously described in the present disclosure.

Additionally, in practice, ECG context recording subcontroller 80 and ECG monitoring module 11 may be in communication to start the recording process based on a user recording prompt inputted into ECG test controller 10 (FIG. 1). Alternatively, ECG context recording subcontroller 80 may start the recording process based on a user recording prompt inputted into ECG context recording controller 80.

Also in practice, ECG context recording controller 80 may further include an ECG context guide module 82 for controlling a playing 23p of a recorded guide video clip 23g stored within video recorder 22 and/or a playing 33p of a record guide video clip 33g stored within audio recorder 32. Recorded guide video clip 23p illustrates a video or a screen to the operator of the ECG test with a list of questions to ask the patient and/or list of actions/movements to be performed by the patient prior to and/or while video clip 21r and/or audio clip 31r is(are) being recorded. Recorded guide audio clip 23g broadcasts to ask clinical questions to the patient and/or list of actions/movements to be performed by the patient prior to and/or while video clip 21r and/or audio clip 31r is(are) being recorded.

Further in practice, for embodiments including an installation of ECG context recording subcontroller 80 within an ECG monitoring device or an ECG therapy device, and an installation of ECG context diagnostic subcontroller 90 within an ECG workstation or an ECG server, ECG context recording module 81 may control a storage of the recorded ECG graph 15g alone with the recorded video clip 21r and/or the recorded audio clip 31r into a storage of or accessible by the ECG workstation or the ECG server.

Still referring to FIG. 2, ECG context recording subcontroller 90 includes a sync file manager 91 and an ECG context diagnostic module 92.

In practice, sync file manager 91 manages a storage retrieval of recorded ECG graph 15g with video clip 21r and/or audio clip 31r.

In one exemplary embodiment, sync file manager 91 manages a storage retrieval of recorded ECG graph 15g from ECG recorder 16 along with a storage retrieval of video clip 21r from video recorder 22 and/or audio clip 31r for audio recorder 22. For example, the exemplary embodiment is applicable to an installation of the recorders 16, 22, 32 and subcontrollers 80, 90 within an ECG monitoring device or an ECG therapy device.

In a second exemplary embodiment, sync file manager 91 manages a storage retrieval of recorded ECG graph 15g from a storage remote from ECG recorder 16 along with a storage retrieval of video clip 21r from the remote storage and/or audio clip 31r from the remote storage. For example, the exemplary embodiment is applicable to an installation of the recorders 16, 22, 32 and subcontroller 80 within an ECG monitoring device or an ECG therapy device, and an installation of subcontroller 90 within an ECG workstation or an ECG server.

Still referring to FIG. 2, upon or subsequent to an opening of a ECG context diagnostic window, ECG context diagnostic module 92 communicates with sync file manager 91 to retrieve the recorded video clip 21r and/or the recorded audio clip 31r to thereby controls a playing of recorded video clip 21r and/or a playing of audio clip 31r within the ECG context diagnostic window simultaneously with a display of the recorded ECG graph 15g within the ECG context diagnostic window.

Figure 3A:
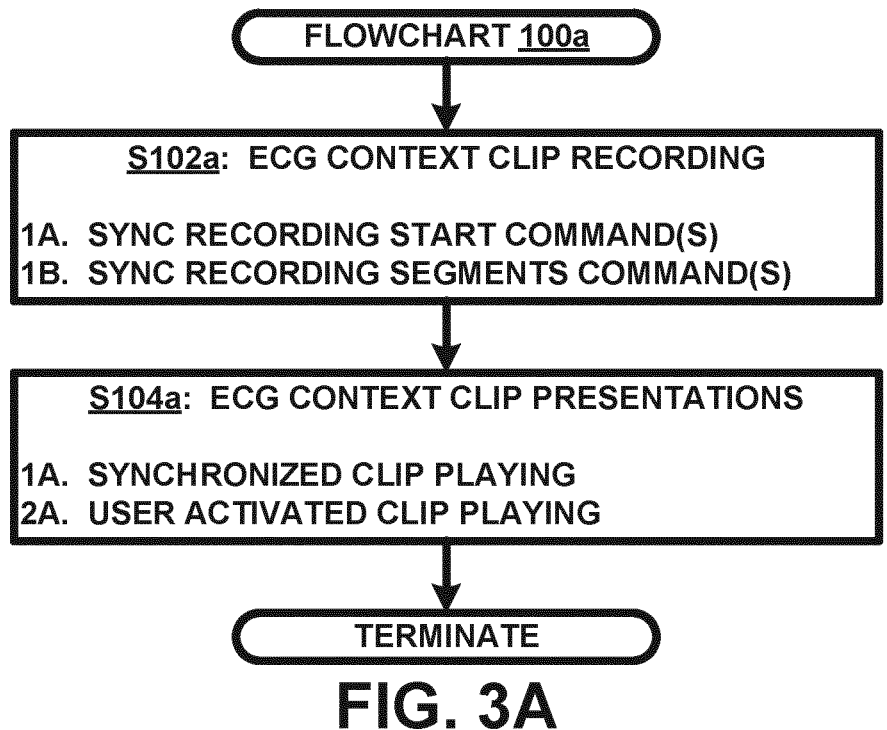
FIG. 3A illustrates a first exemplary embodiment of flowchart representative of an ECG context testing and diagnostic method in accordance with the present disclosure.
Figure 3B:
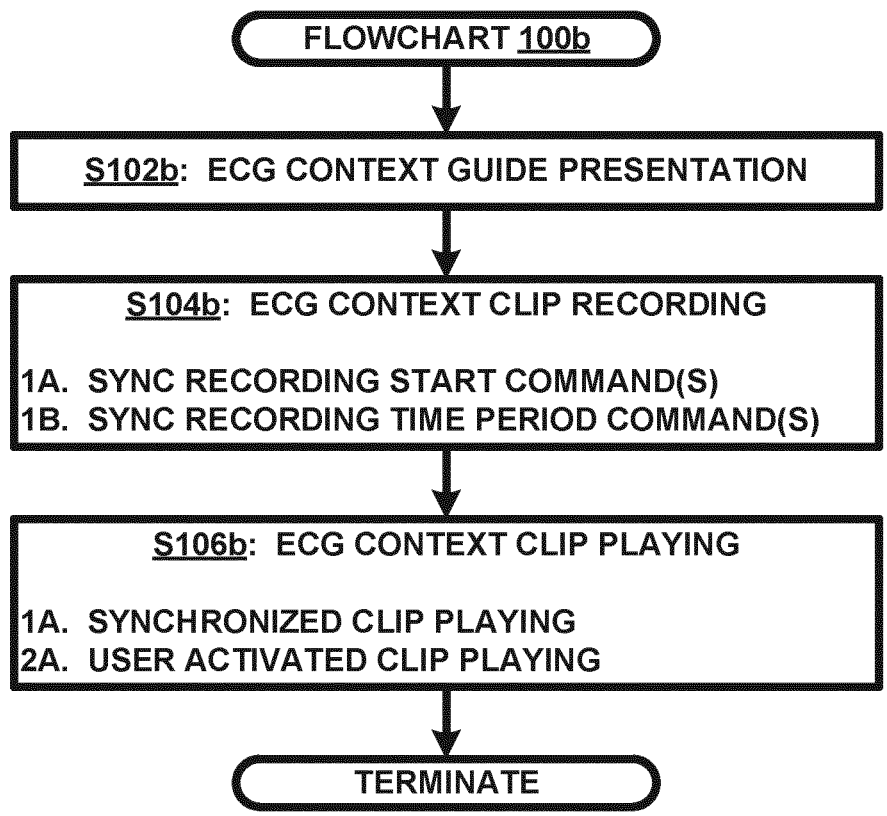
FIG. 3B illustrates a second exemplary embodiment of flowchart representative of an ECG context testing and diagnostic method in accordance with the present disclosure.

FIGS. 3A and 3B respectively illustrates a flowchart 100a and a flowchart 100b representative of two (2) exemplary embodiments of a ECG context method of the present disclosure executable by subcontrollers 80 and 90 of FIG. 2.

Referring to FIGS. 2 and 3A, upon a display of a ECG context recording window by ECG monitoring module 11 (FIG. 1), a stage S102a of flowchart 100a encompasses ECG context recording module 81 of ECG context recording subcontroller 80 commanding a recording start of video recorder 22 of video transmission 21t and/or a recording start of audio recorder 32 of an audio transmission 31t in sync with a recording start of ECG recorder 16 of ECG lead signals 15s by ECG monitoring module 11 whereby module 81 commands a recording stop a recording stop of video recorder 22 of video transmission 21t and/or a recording stop of audio recorder 32 of an audio transmission 31t prior to or in sync with a recording stop of ECG recorder 16 of ECG lead signals 15s by ECG monitoring module 11.

Alternatively, upon a display of a ECG context window by ECG monitoring module 11, a stage S102a of flowchart 100a encompasses ECG context recording module 81 of ECG context recording subcontroller 80 commands a recording start of video recorder 22 of video transmission 21t and/or a recording start of audio recorder 32 of an audio transmission 31t in sync with a specified time segment ECG lead signals 15s subsequent to a recording start of ECG recorder 16 of ECG lead signals 15s by ECG monitoring module 11.

Figure 4A:
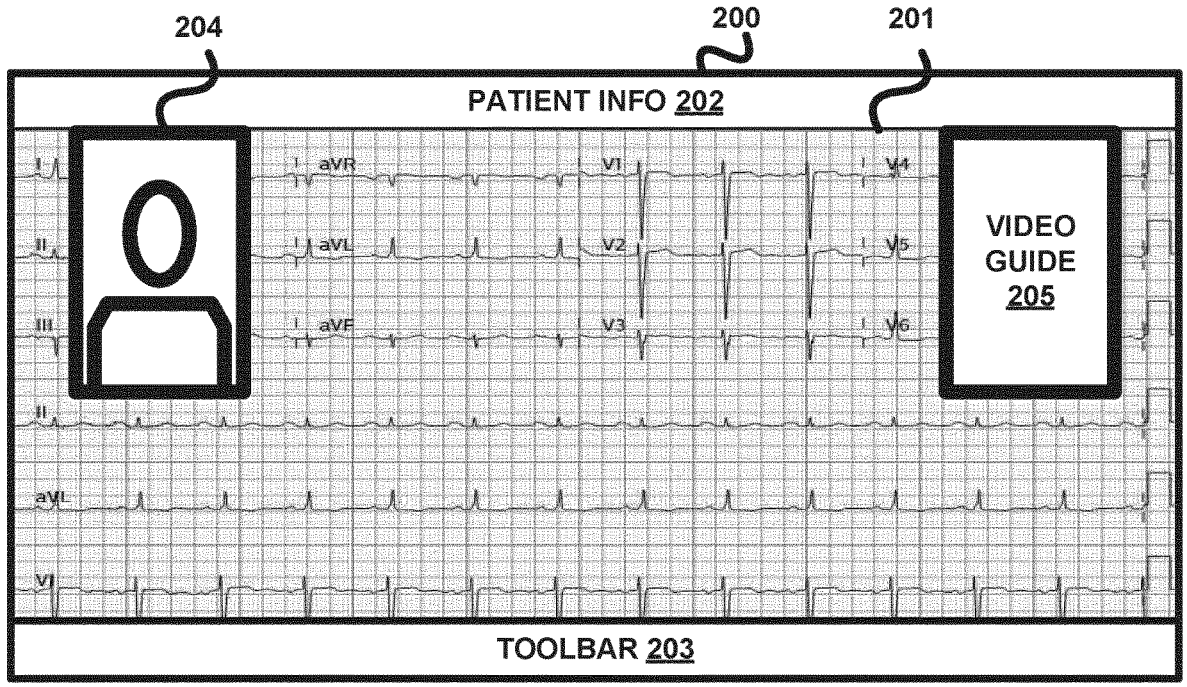
FIG. 4A illustrates an exemplary embodiment of ECG context recording window in accordance with the present disclosure.

FIG. 4A illustrates an exemplary ECG context recording window 200 an ECG graph display 201, a patient info area 202, a toolbar 203 and a playing 204 of the video transmission 21t.

Referring back to FIGS. 2A and 3A, subsequently upon a display of a ECG context diagnostic window by ECG diagnostic module 12 (FIG. 1), a stage S104a of flowchart 100a encompasses ECG diagnostic recording module 92 of ECG context diagnostic subcontroller 90 commanding a playing of the recorded video clip 21r and/or a playing of the recorded audio clip 31r in sync with a display of the recorded ECG graph 15s. A timing sync marker may be used to display the start time and/or the end time of the recorded video clip 21r and/or a playing of the recorded audio clip 31r in synchronization of ECG graph 15s.

Alternatively, subsequently upon a display of a ECG context diagnostic window by ECG diagnostic module 12, stage S104a of flowchart 100a encompasses ECG diagnostic recording module 92 of ECG context diagnostic subcontroller 90 commanding a playing of the recorded video clip 21r and/or a playing of the recorded audio clip 31r in response to a user activation of the recordings 21r and/or 31r. For example, the user may utilize a diagnostic tool for the displayed ECG graph 15g, which would prompt a playing of the recorded video clip 21r and/or a playing of the recorded audio clip 31r. A timing sync marker may be used to display the start time and/or the end time of the recorded video clip 21r and/or a playing of the recorded audio clip 31r in synchronization of ECG graph 15s.

Also in practice, ECG context recording module 81 may implement a search engine of the video clip and/or audio clip to determine when the patient may have called out when a symptomatic event occurred whereby the timing of the video and audio symptoms may be further synched during stage S102a to the exact point of time of the corresponding abnormality in the ECG graph (e.g., a short burst of arrhythmia). This provides clinical context of timing and description of symptoms during the display of a ECG context diagnostic window during stage S104a, particularly with a symptom sync marker delineating the timing and description of symptoms within the video clip and/or the audio clip.

Alternatively, an operator of the system may input a timing of when the patient may have described an occurrence of a symptomatic event (e.g., via a mouse, a hand clicker, etc.). Again, a symptom sync marker delineating the timing and description of symptoms within the video clip and/or the audio clip may be displayed in the ECG context diagnostic window.

Further in practice, audio clip 31r may be transcribed into a text that is displayed within the ECG context diagnostic window. Additionally, word(s) of the text may be highlighted/italicized or colored as the word(s) is(are) being spoken. Additionally, ECG diagnostic recording module 92 may link text to the timing of the ECG graph 15g whereby any user interaction with the text highlight a view window over a synched segment of the ECG graph 15g.

Figure 4B:
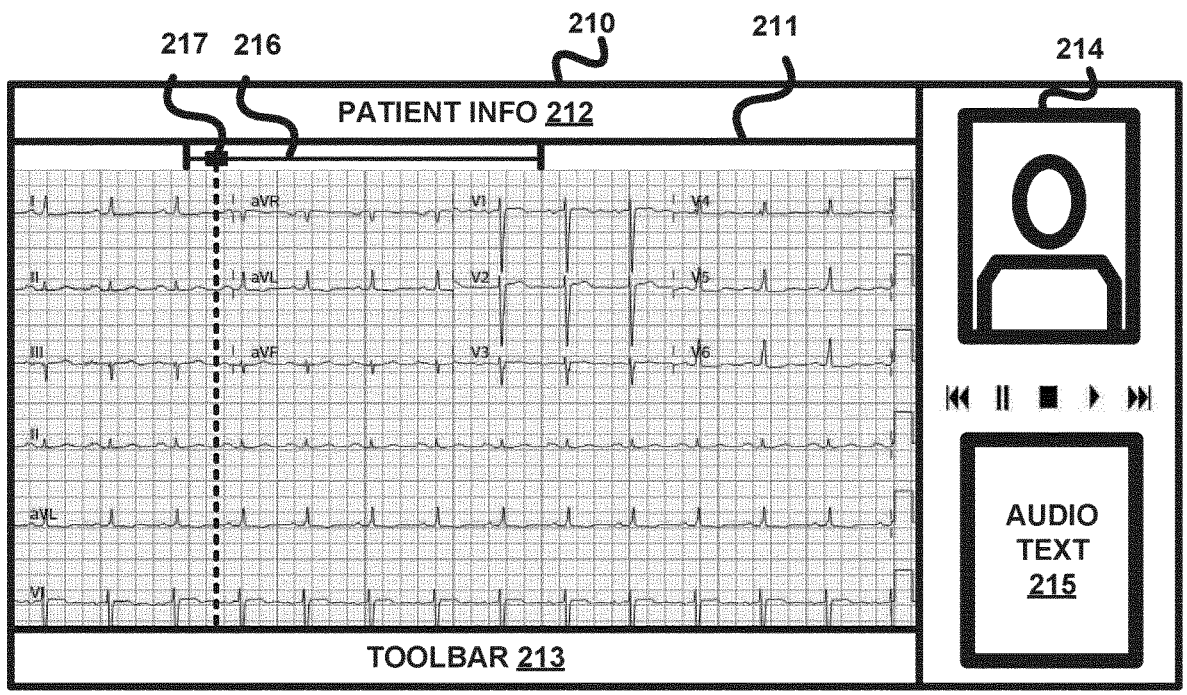
FIG. 4B illustrates an exemplary embodiment of an ECG context diagnostic window in accordance with the present disclosure.

FIG. 4B illustrates an exemplary ECG context recording window 210 includes an ECG graph display 211, a patient info area 212, a toolbar 213, a video frame 214 for the recorded video clip 21r.

Additionally, ECG context recording window 210 includes an audio frame 215 for audio text, a time sync marker 216 highlighting the start and end sync times of the recorded video clip 21r and the recorded audio clip 31r, and a symptom sync marker 217 highlighting an occurrence of a description of the symptomatic event by the patient.

Referring to FIGS. 2 and 3B, a stage S104b and a stage 106b of a flowchart 100b are identical to respective stages S102a and S104a as previously described in the present disclosure. Flowchart 100b includes an additional stage S102b for playing video guide 23g prior to or concurrently with a playing of video clip 21r during stage S102a and/or for playing audio guide 33g prior to or concurrently with a playing of audio clip 31r during stage S102a.

Figure 5:
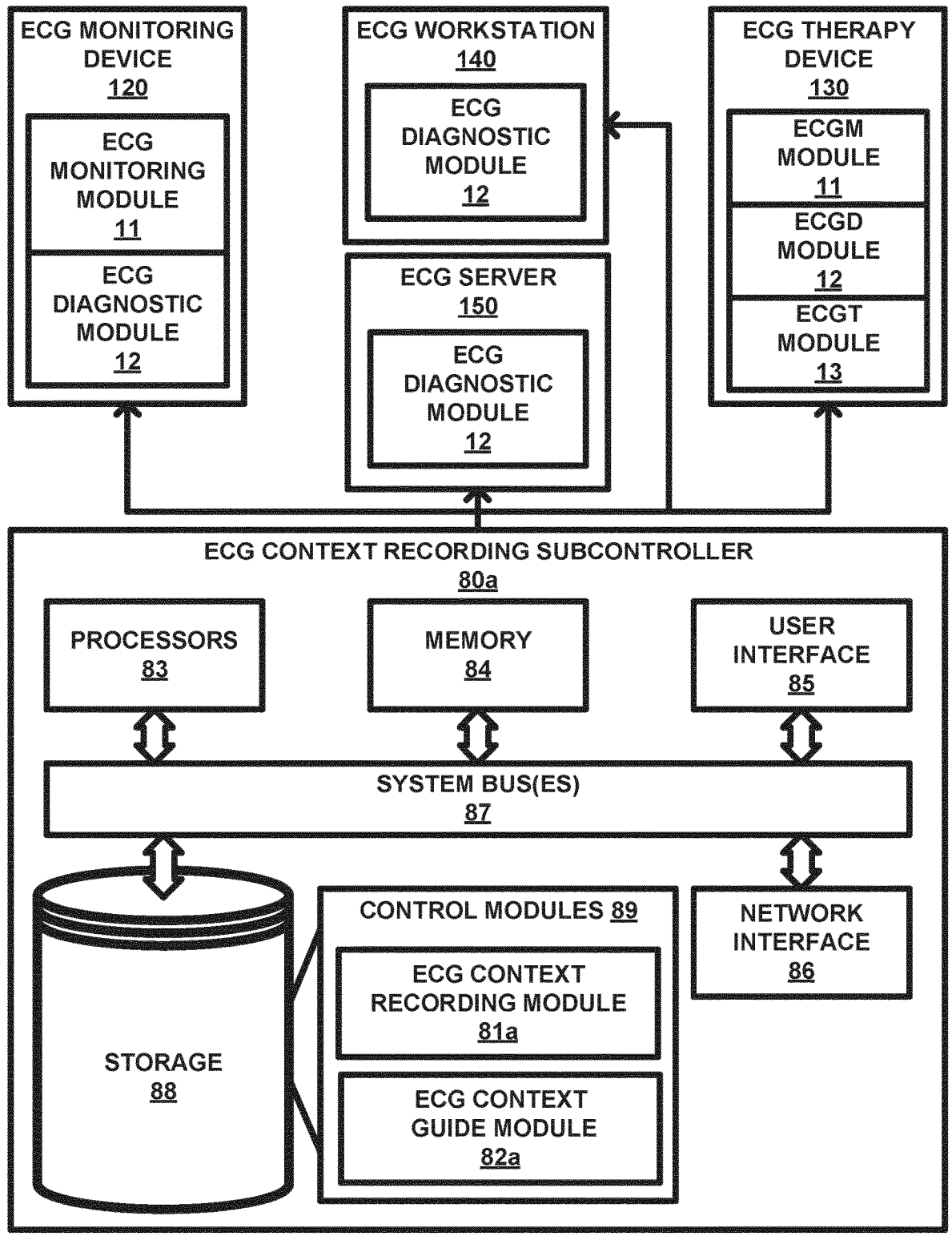
FIG. 5 illustrates an exemplary embodiment of an ECG context recording subcontroller in accordance with the present disclosure.

Referring to FIG. 5, an exemplary embodiment 80a of ECG context recording subcontroller 80 (FIG. 2) includes one or more processor(s) 83, memory 84, a user interface 85, a network interface 86, and a storage 88 interconnected via one or more system buses 87.

Each processor 83 may be any hardware device, as known in the art of the present disclosure or hereinafter conceived, capable of executing instructions stored in memory 84 or storage or otherwise processing data. In a non-limiting example, the processor(s) 83 may include a microprocessor, field programmable gate array (FPGA), application-specific integrated circuit (ASIC), or other similar devices.

The memory 84 may include various memories, as known in the art of the present disclosure or hereinafter conceived, including, but not limited to, L1, L2, or L3 cache or system memory. In a non-limiting example, the memory 84 may include static random access memory (SRAM), dynamic RAM (DRAM), flash memory, read only memory (ROM), or other similar memory devices.

The user interface 85 may include one or more devices, as known in the art of the present disclosure or hereinafter conceived, for enabling communication with a user such as an administrator. In a non-limiting example, the user interface may include a command line interface or graphical user interface that may be presented to a remote terminal via the network interface 86.

The network interface 86 may include one or more devices, as known in the art of the present disclosure or hereinafter conceived, for enabling communication with other hardware devices. In a non-limiting example, the network interface 86 may include a network interface card (NIC) configured to communicate according to the Ethernet protocol. Additionally, the network interface 86 may implement a TCP/IP stack for communication according to the TCP/IP protocols. Various alternative or additional hardware or configurations for the network interface 86 will be apparent.

The storage 88 may include one or more machine-readable storage media, as known in the art of the present disclosure or hereinafter conceived, including, but not limited to, read-only memory (ROM), random-access memory (RAM), magnetic disk storage media, optical storage media, flash-memory devices, or similar storage media. In various non-limiting embodiments, the storage 88 may store instructions for execution by the processor(s) 83 or data upon with the processor(s) 83 may operate. For example, the storage 88 may store a base operating system for controlling various basic operations of the hardware. The storage 88 also stores application modules in the form of executable software/firmware for implementing the various functions of the subcontroller 80a as previously described in the present disclosure including, but not limited to, an ECG context recording module 81a and an ECG context guide module 82a as previously described in the present disclosure.

In practice, subcontroller 80a may be installed within an ECG monitoring device 120, an ECG therapy device 130, an ECG workstation 140 and an ECG server 141.

Figure 6:
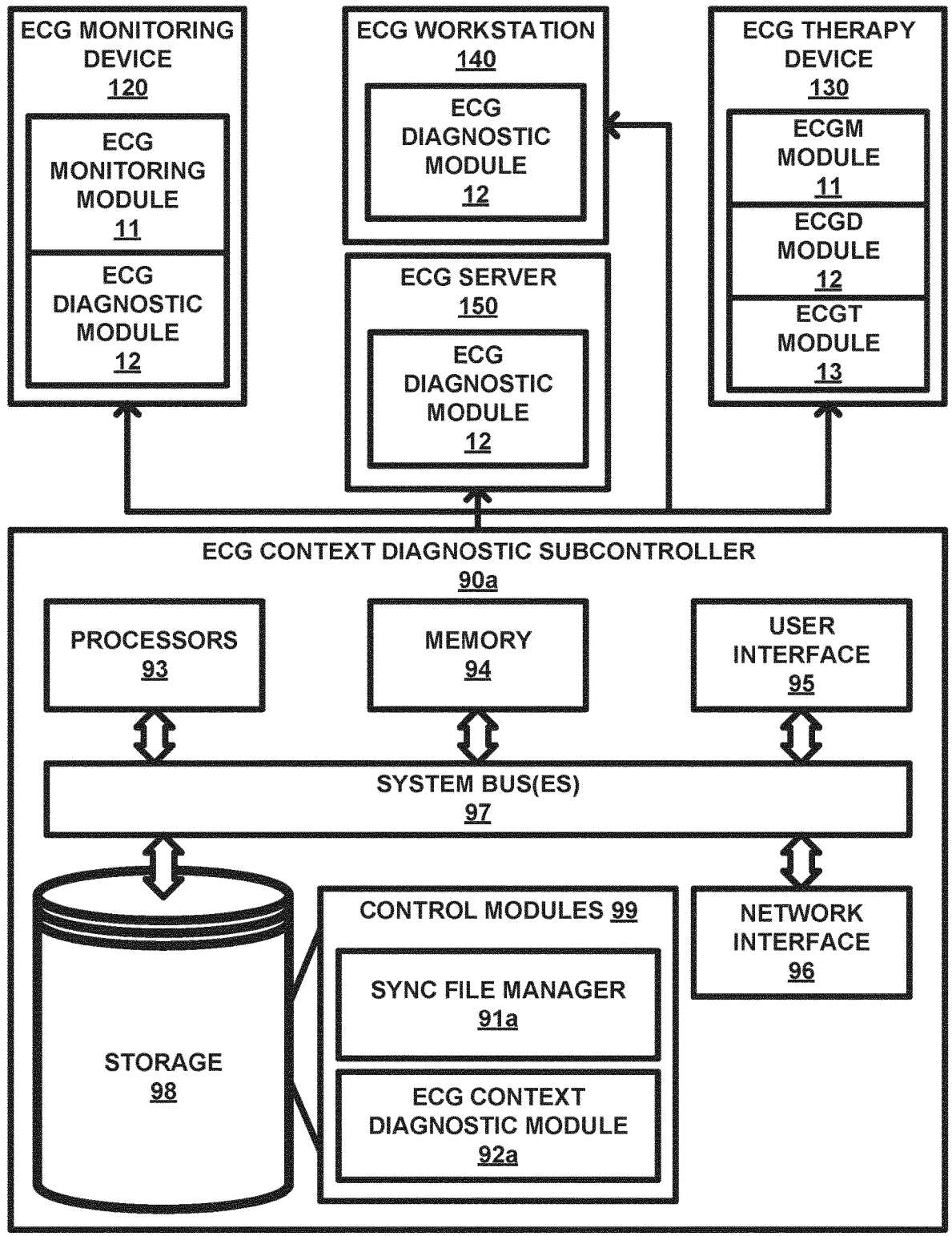
FIG. 6 illustrates an exemplary embodiment of an ECG context diagnostic subcontroller in accordance with the present disclosure.

Referring to FIG. 6, an exemplary embodiment 90a of ECG context diagnostic subcontroller 90 (FIG. 2) includes one or more processor(s) 93, memory 94, a user interface 95, a network interface 96, and a storage 98 interconnected via one or more system buses 97.

Each processor 93 may be any hardware device, as known in the art of the present disclosure or hereinafter conceived, capable of executing instructions stored in memory 94 or storage or otherwise processing data. In a non-limiting example, the processor(s) 93 may include a microprocessor, field programmable gate array (FPGA), application-specific integrated circuit (ASIC), or other similar devices.

The memory 94 may include various memories, as known in the art of the present disclosure or hereinafter conceived, including, but not limited to, L1, L2, or L3 cache or system memory. In a non-limiting example, the memory 94 may include static random access memory (SRAM), dynamic RAM (DRAM), flash memory, read only memory (ROM), or other similar memory devices.

The user interface 95 may include one or more devices, as known in the art of the present disclosure or hereinafter conceived, for enabling communication with a user such as an administrator. In a non-limiting example, the user interface may include a command line interface or graphical user interface that may be presented to a remote terminal via the network interface 96.

The network interface 96 may include one or more devices, as known in the art of the present disclosure or hereinafter conceived, for enabling communication with other hardware devices. In a non-limiting example, the network interface 96 may include a network interface card (NIC) configured to communicate according to the Ethernet protocol. Additionally, the network interface 96 may implement a TCP/IP stack for communication according to the TCP/IP protocols. Various alternative or additional hardware or configurations for the network interface 96 will be apparent.

The storage 98 may include one or more machine-readable storage media, as known in the art of the present disclosure or hereinafter conceived, including, but not limited to, read-only memory (ROM), random-access memory (RAM), magnetic disk storage media, optical storage media, flash-memory devices, or similar storage media. In various non-limiting embodiments, the storage 98 may store instructions for execution by the processor(s) 93 or data upon with the processor(s) 93 may operate. For example, the storage 98 may store a base operating system for controlling various basic operations of the hardware. The storage 98 also stores application modules in the form of executable software/firmware for implementing the various functions of the subcontroller 91a as previously described in the present disclosure including, but not limited to, a sync file manager 91a and an ECG context diagnostic module 92a as previously described in the present disclosure.

In practice, subcontroller 90a may be installed within an ECG monitoring device 120, an ECG therapy device 130, an ECG workstation 140 and an ECG server 150.

To facilitate a further understanding of the present disclosure, the following description of FIGS. 7A-7E teaches exemplary embodiments of an ECG context devices and systems in accordance with the present disclosure. From the description of FIG. 2, those having ordinary skill in the art of the present disclosure will appreciate how to apply the present disclosure to make and use additional embodiments of an ECG context devices and systems in accordance with the present disclosure.

Figure 7A:
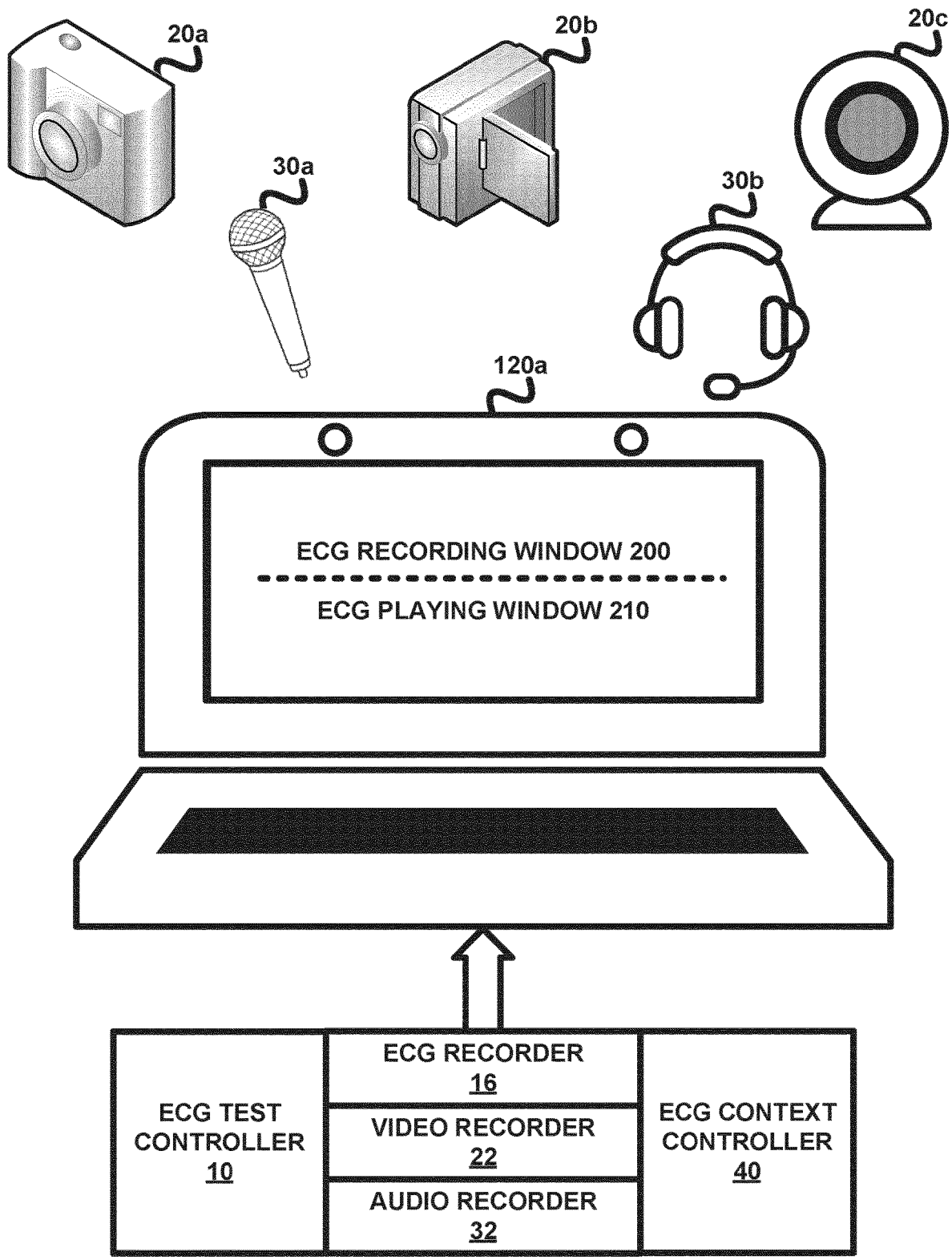
FIG. 7A illustrates a first exemplary embodiment of an ECG context testing and diagnostic system in accordance with the present disclosure.

FIG. 7A illustrates an ECG monitoring device 120a. In one exemplary embodiment, ECG monitoring device 120a employs a digital camera 20a as a video source and a microphone 30a as an audio source, both installed within ECG monitoring device 120a. In a second exemplary embodiment, ECG monitoring device 120a employs a digital camcorder as a video/audio source externally coupled to ECG monitoring device 120a via a platform arm (not shown). In a third exemplary embodiment, ECG monitoring device 120a employs a webcam 20c as an video source and a headset 30b as an audio source, both being pluggable into ECG monitoring device 120a.

For ECG testing and diagnostic purposes, ECG monitoring device 120a has ECG testing controller 10, ECG recorder 16, video recorder 22, audio recorder 32 and ECG context controller 40 as previously described in the present disclosure. In operation, during a testing phase of the ECG monitoring, ECG monitoring device 120a displays an ECG context recording window 200 (FIG. 4A) and controls a synchronized recording the ECG graph, the video clip and the audio clip as previously described in the present disclosure. During a subsequent diagnostic phase of the ECG monitoring, ECG monitoring device 120a displays an ECG context diagnostic window 210 (FIG. 4B) of the recorded ECG graph with a simultaneous playing of the recorded video clip and the recorded audio clip as previously described in the present disclosure.

Figure 7B:
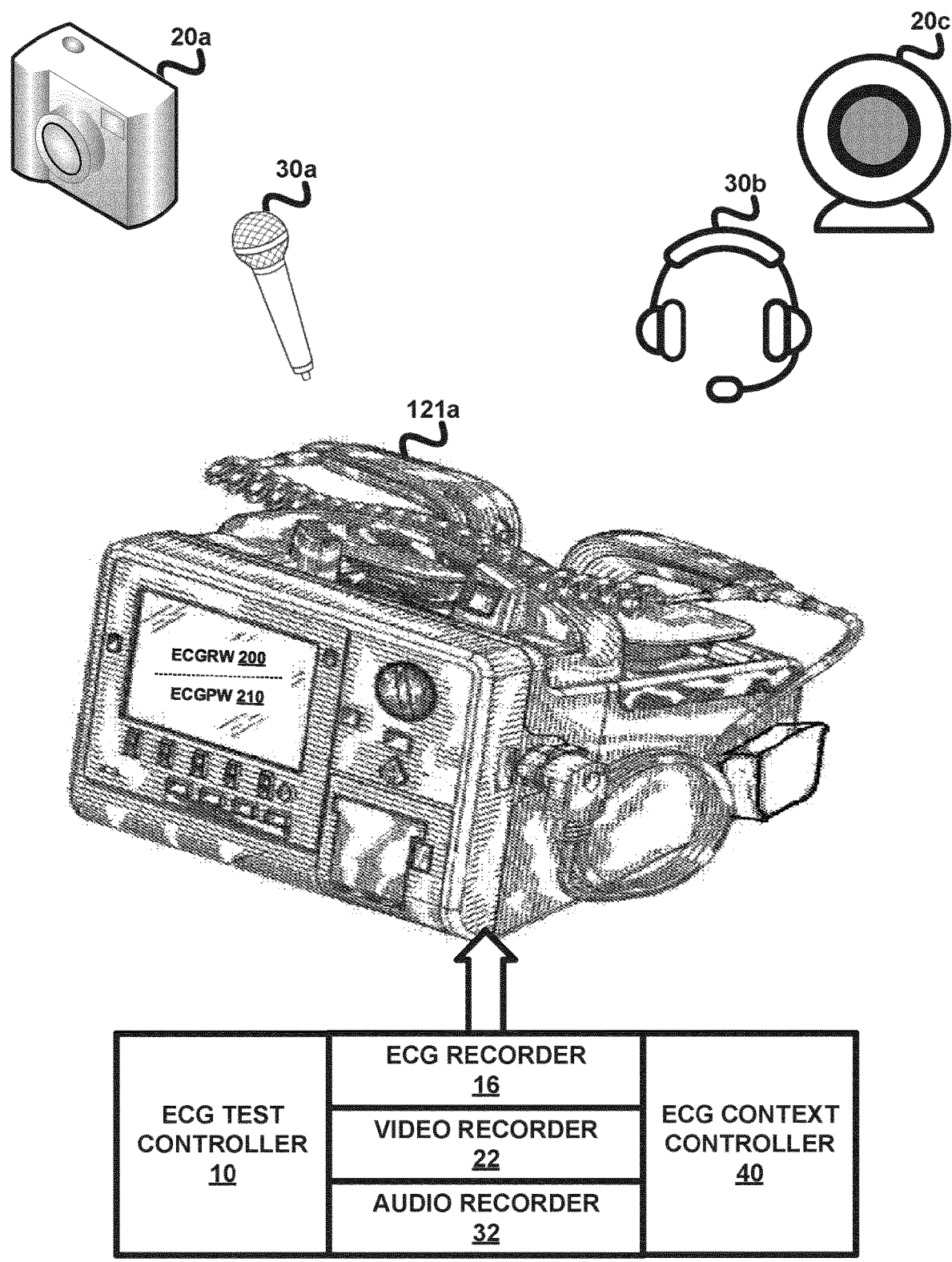
FIG. 7B illustrates a second exemplary embodiment of an ECG context testing and diagnostic system in accordance with the present disclosure.

FIG. 7B illustrates an ECG therapy device 130a. In one exemplary embodiment, ECG therapy device 130a employs a digital camera 20a as a video source and a microphone 30a as an audio source, both installed within ECG monitoring device 102. In a second exemplary embodiment, ECG monitoring device 102 employs a digital camcorder as a video/audio source externally coupled to ECG monitoring device 102 via a platform arm (not shown). In a third exemplary embodiment, ECG monitoring device 102 employs a webcam 20c as an video source and a headset 30b as an audio source, both being pluggable into ECG monitoring device 102.

For ECG testing and diagnostic purposes, ECG therapy device 130a has ECG testing controller 10, ECG recorder 16, video recorder 22, audio recorder 32 and ECG context controller 40 as previously described in the present disclosure. In operation, during a testing phase of the therapy, ECG therapy device 130a displays an ECG context recording window 200 (FIG. 4A) and controls a synchronized recording the ECG graph, the video clip and the audio clip as previously described in the present disclosure. During a subsequent diagnostic phase of the ECG therapy, ECG therapy device 130a displays an ECG context diagnostic window 210 (FIG. 4B) of the recorded ECG graph with a simultaneous playing of the recorded video clip and the recorded audio clip as previously described in the present disclosure.

Figure 7C:
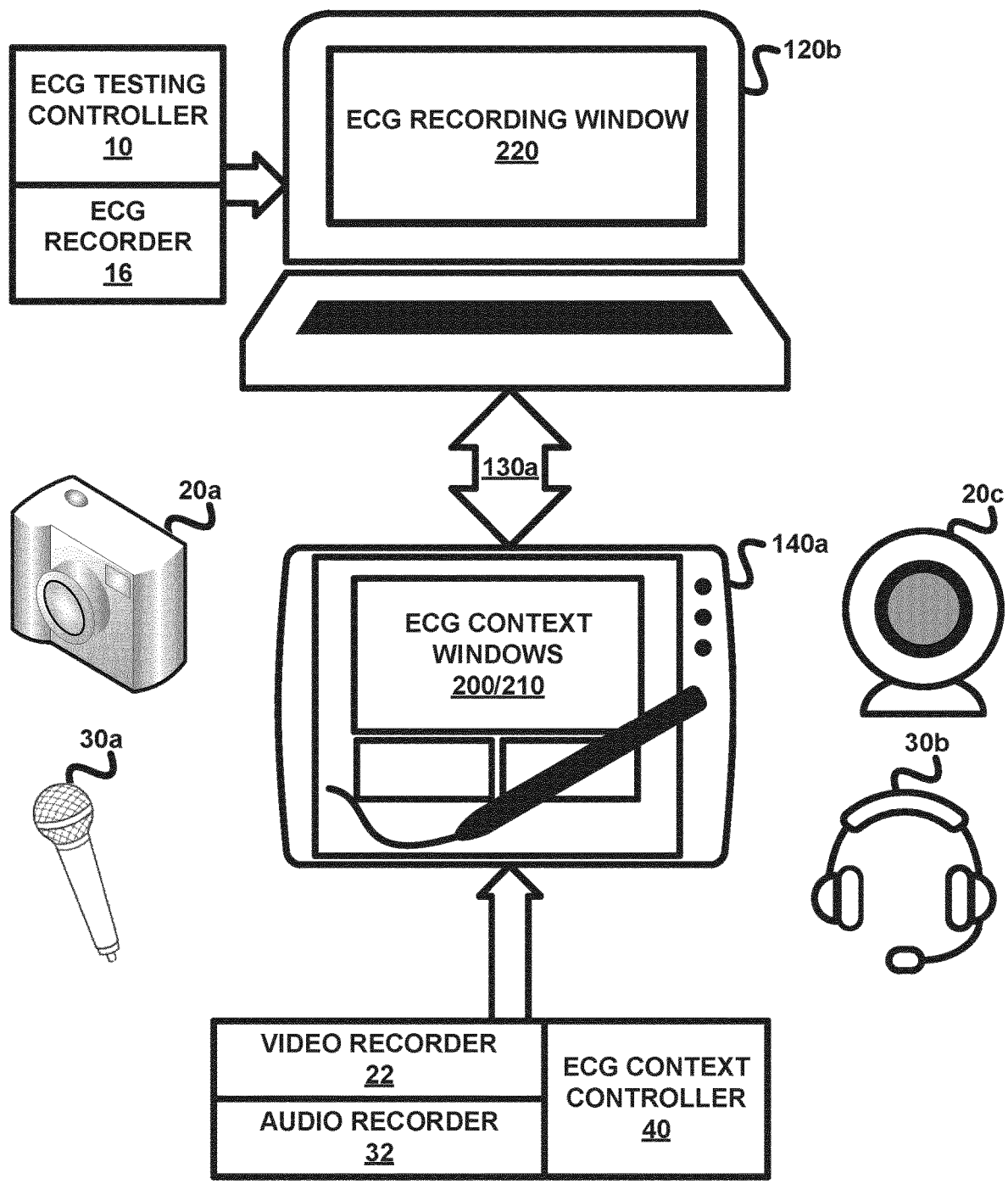
FIG. 7C illustrates a third exemplary embodiment of an ECG context testing and diagnostic system in accordance with the present disclosure.

FIG. 7C illustrates an ECG monitoring device 120b and an ECG workstation 140a (e.g., a tablet). In one exemplary embodiment, ECG workstation 140a employs a digital camera 20a as a video source and a microphone 30a as an audio source, both installed within ECG monitoring device 102. In a second exemplary embodiment, ECG workstation 140a employs a web cam 20c as an video source and a headset 30b as an audio source, both being pluggable into ECG workstation 140a.

For ECG testing purposes, ECG monitoring device 120b has ECG testing controller 10 and ECG recorder 16 as previously described in the present disclosure.

For ECG diagnostic purposes, ECG workstation 140a has video recorder 22, audio recorder 32 and ECG context controller 40 as previously described in the present disclosure.

In operation, a communication channel 130 as is established whereby ECG workstation 140a may stream the recorded ECG graph 15g.

During a testing phase of the ECG monitoring, ECG monitoring device 102 controls a recording of the ECG graph as displayed in a ECG recording window 220 as known in the art of the present disclosure of the ECG graph, and ECG workstation 140a displays an ECG context recording window 200 (FIG. 4A) showing the streamed ECH graph while controlling a synchronized recording the video clip and/or the audio clip.

During a subsequent ECG diagnostic phase of the ECG monitoring, ECG workstation 140a displays ECG context diagnostic window 210 (FIG. 4B) of the recorded ECG graph with a simultaneous playing of the recorded video clip and the recorded audio clip as previously described in the present disclosure.

Figure 7D:
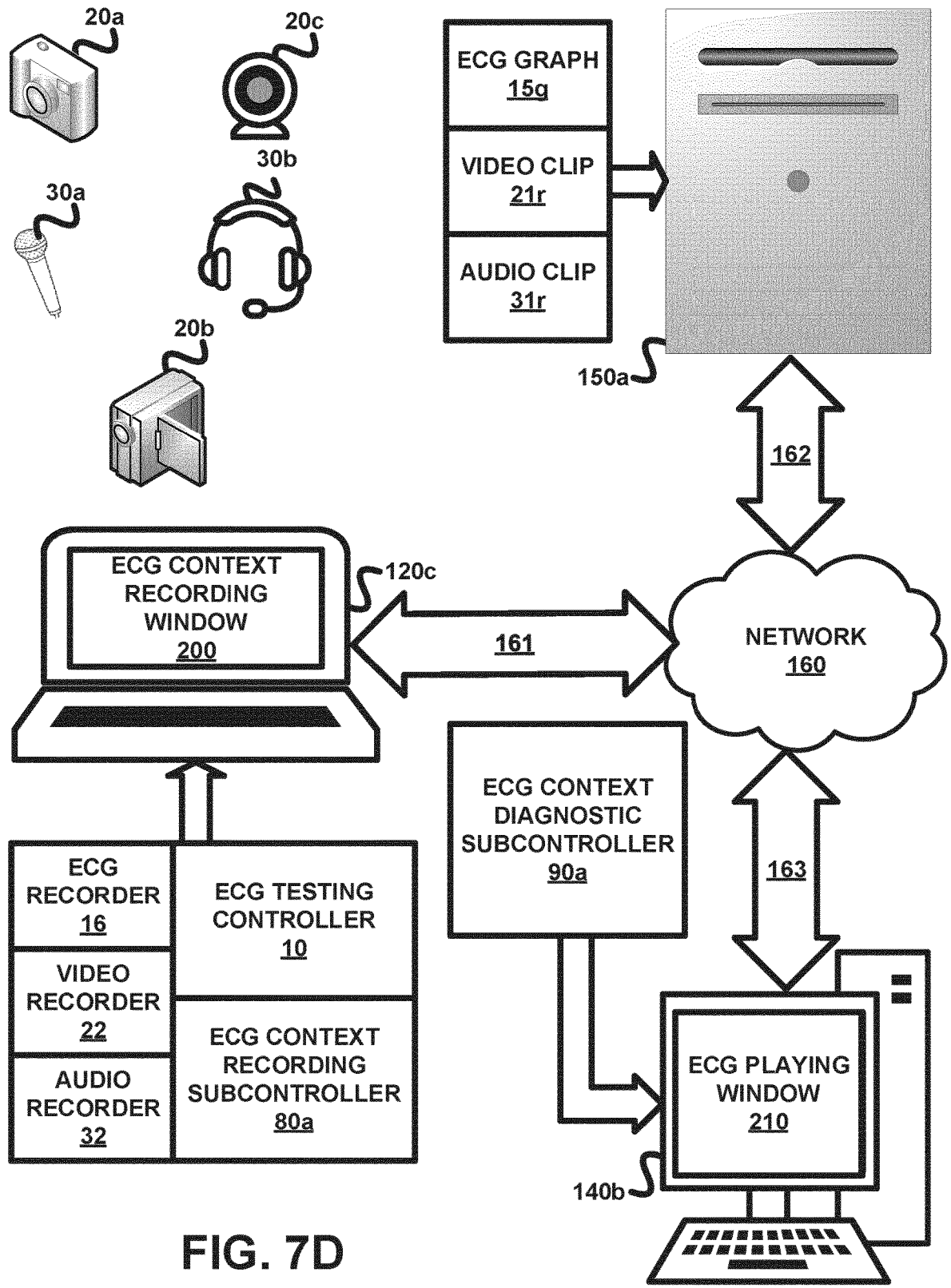
FIG. 7D illustrates a fourth exemplary embodiment of an ECG context testing and diagnostic system in accordance with the present disclosure.

FIG. 7D illustrates an ECG monitoring device 120c, an ECG workstation 140b (e.g., a desktop PC) and an ECG server 150a. In one exemplary embodiment, ECG monitoring device 120c employs a digital camera 20a as a video source and a microphone 30a as an audio source, both installed within ECG monitoring device 120c. In a second exemplary embodiment, monitoring device 120c employs a digital camcorder as a video/audio source externally coupled to monitoring device 120c via a platform arm (not shown). In a third exemplary embodiment, monitoring device 120c employs a webcam 20c as an video source and a headset 30b as an audio source, both being pluggable into monitoring device 120b.

For ECG testing and diagnostic purposes, a network 160 has communication channels 16-163 for illustrates ECG monitoring device 120c, an ECG workstation 140b and ECG server 150a. ECG monitoring device 120c has ECG testing controller 10, ECG recorder 16a, video recorder 22a, audio recorder 32a and ECG context recording subcontroller 80a as previously described in the present disclosure. ECG workstation 140b has ECG context diagnostic sub controller 90a as previously described in the present disclosure.

In operation, during a testing phase of the ECG monitoring, ECG monitoring device 120c displays an ECG context recording window 200 (FIG. 4A) and controls a synchronized recording of the ECG graph, the video clip and the audio clip as previously described in the present disclosure. Additionally, subcontroller 80a controls a remote storage of the recorded ECG graph 15s, the recorded video clip 21r and the recorded audio clip 31r into ECG server 150a.

During a subsequent diagnostic phase of the ECG monitoring, subcontroller 90a retrieves the recorded ECG graph 15s, the recorded video clip 21r and the recorded audio clip 31r from ECG server 150a, and ECG workstation 140a displays an ECG context diagnostic window 210 (FIG. 4B) of the recorded ECG graph 15g with a simultaneous playing of the recorded video clip 21r and the recorded audio clip 31r as previously described in the present disclosure.

Figure 7E:
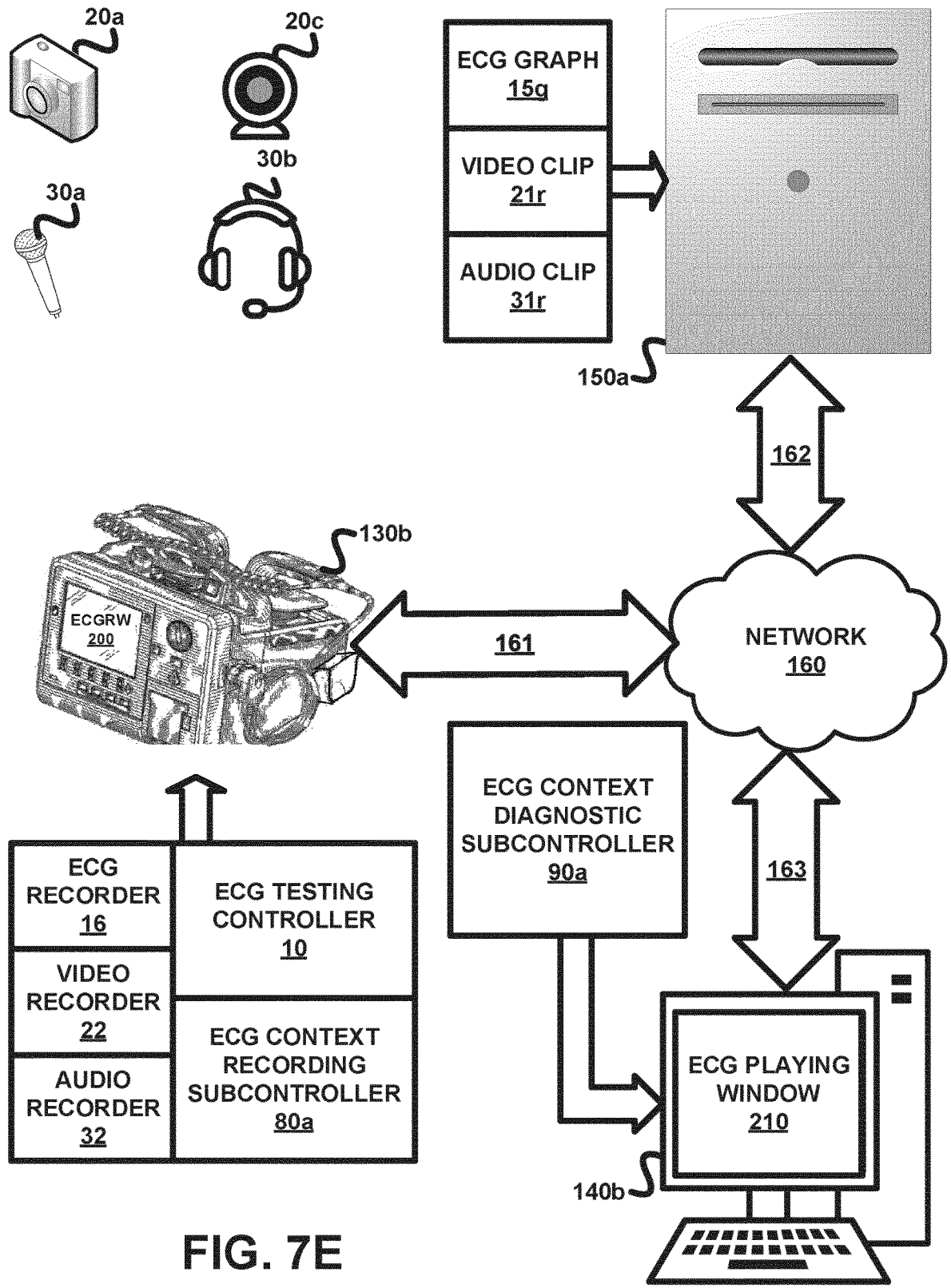
FIG. 7E illustrates a fifth exemplary embodiment of an ECG context testing and diagnostic system in accordance with the present disclosure

FIG. 7E illustrates an ECG therapy device 130b, an ECG workstation 140b (e.g., a desktop PC) and an ECG server 150a. In one exemplary embodiment, ECG therapy device 130b employs a digital camera 20a as a video source and a microphone 30a as an audio source, both installed within ECG therapy device 130b. In a second exemplary embodiment, ECG therapy device 130b employs a webcam 20c as an video source and a headset 30b as an audio source, both being pluggable into ECG therapy device 130b.

For ECG testing and diagnostic purposes, a network 160 has communication channels 16-163 for illustrates ECG therapy device 130b, an ECG workstation 140b and ECG server 150a. ECG therapy device 130b has ECG testing controller 10, ECG recorder 16a, video recorder 22a, audio recorder 32a and ECG context recording sub controller 80a as previously described in the present disclosure. ECG workstation 140b has ECG context diagnostic subcontroller 90a as previously described in the present disclosure.

In operation, during a testing phase of the ECG monitoring, ECG therapy device 130b displays an ECG context recording window 200 (FIG. 4A) and controls a synchronized recording of the ECG graph, the video clip and the audio clip as previously described in the present disclosure. Additionally, subcontroller 80a controls a remote storage of the recorded ECG graph 15s, the recorded video clip 21r and the recorded audio clip 31r into ECG server 150a.

During a subsequent diagnostic phase of the ECG monitoring, subcontroller 90a retrieves the recorded ECG graph 15s, the recorded video clip 21r and the recorded audio clip 31r from ECG server 150a, and ECG workstation 140a displays an ECG context diagnostic window 210 (FIG. 4B) of the recorded ECG graph 15g with a simultaneous playing of the recorded video clip 21r and the recorded audio clip 31r as previously described in the present disclosure.

Referring to FIGS. 1-7E, those having ordinary skill in the art of the present disclosure will appreciate numerous benefits of the present disclosure including, but not limited to, an ECG test within a relevant clinical context.

Further, as one having ordinary skill in the art will appreciate in view of the teachings provided herein, structures, elements, components, etc. described in the present disclosure/specification and/or depicted in the Figures may be implemented in various combinations of hardware and software, and provide functions which may be combined in a single element or multiple elements. For example, the functions of the various structures, elements, components, etc. shown/illustrated/depicted in the Figures can be provided through the use of dedicated hardware as well as hardware capable of executing software in association with appropriate software for added functionality. When provided by a processor, the functions can be provided by a single dedicated processor, by a single shared processor, or by a plurality of individual processors, some of which can be shared and/or multiplexed. Moreover, explicit use of the term "processor" or "controller" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Having described preferred and exemplary embodiments of the various and numerous inventions of the present disclosure (which embodiments are intended to be illustrative and not limiting), it is noted that modifications and variations can be made by persons skilled in the art in light of the teachings provided herein, including the Figures. It is therefore to be understood that changes can be made in/to the preferred and exemplary embodiments of the present disclosure which are within the scope of the embodiments disclosed herein.

Moreover, it is contemplated that corresponding and/or related systems incorporating and/or implementing the device/system or such as may be used/implemented in/with a device in accordance with the present disclosure are also contemplated and considered to be within the scope of the present disclosure. Further, corresponding and/or related method for manufacturing and/or using a device and/or system in accordance with the present disclosure are also contemplated and considered to be within the scope of the present disclosure.

The invention claimed is:

1. An ECG control network, comprising:
    an ECG context controller configured to control:
        a synchronization of a recording of an ECG test by an ECG test controller with at least one of a recording of a video clip illustrative of a clinical context of the ECG test and a recording of an audio clip informative of the clinical context of the ECG test; and
        a simultaneous presentation of a displaying of recording of the ECG test with at least one of a playing of the video clip and a playing of the audio clip, wherein the presentation includes an ECG graph display and a toolbar,
        wherein the ECG context controller is further configured to record a symptom sync marker based on user input during the ECG test, indicative of a timing of a user describing occurrence of a symptomatic event during the ECG test, and wherein the symptom sync marker is further presented during said simultaneous presentation.

2. The ECG control network of claim 1, further comprising an ECG test controller, wherein the ECG test controller is installed within one of an ECG monitoring device or an ECG therapy device; and wherein the ECG context controller is installed within one or distributed among the ECG monitoring device, the ECG therapy device, an ECG workstation and an ECG server.

3. The ECG control network of claim 1, wherein the ECG context controller includes:

an ECG context recording subcontroller configured to synchronize the at least one of the recording of the video clip and the recording of the audio clip to a specified time period of the recording of the ECG test.

4. The ECG control network of claim 3, wherein the ECG context recording subcontroller is configured, in communication with at least one of a video source and an audio source, to control one of:

a video transmission by the video source illustrative of the clinical context of the ECG test during the specified time period of the recording of the ECG test; and an audio transmission by the audio source illustrative of the clinical context of the ECG test during the specified time period of the recording of the ECG test.

5. The ECG control network of claim 3, wherein the ECG context recording subcontroller is configured, in communication with at least one of a video recorder and an audio recorder, to control one of:

the recording of the video clip by the video recorder during the specified time period of the recording of the ECG test; and the recording of the audio clip by the audio recorder during the specified time period of the recording of the ECG test.

6. The ECG control network of claim 1, wherein the ECG context controller includes:

an ECG context diagnostic subcontroller configured to control a displaying of an ECG context window illustrating the recording of the ECG test.

7. The ECG control network claim 1, wherein the ECG context controller includes:

an ECG context diagnostic subcontroller configured to control one of:

an automatic playing of the video clip in synchronization with an opening of an ECG context window illustrating the recording of the ECG test; and an automatic playing of the audio clip in synchronization with the opening of the ECG context window illustrating the recording of the ECG test.

8. The ECG control network claim 1, wherein the ECG context controller includes:

an ECG context diagnostic subcontroller configured to control one of:

an automatic playing of the video clip in response to a user interaction with the recording of the ECG test as illustrated in an ECG context window; and an automatic playing of the audio clip in response to the user interaction with the recording of the ECG test as illustrated in the ECG context window.

9. An ECG context controller, comprising:

an ECG context recording subcontroller configured to control a synchronization of a recording of an ECG test with at least one of a recording of a video clip illustrative of a clinical context of the ECG test and a recording of an audio clip informative of the clinical context of the ECG test; and an ECG context diagnostic subcontroller configured, in communication with the ECG context recording subcontroller, to control a simultaneous presentation of a displaying of the recording of the ECG test with at least one of a playing of the video clip and a playing of the audio clip, wherein the presentation includes an ECG graph display and a toolbar, and wherein the ECG context controller is configured to record a symptom sync marker based on user input during the ECG test, indicative of a timing of a user describing occurrence of a symptomatic event during the ECG test, and wherein the symptom sync marker is further presented during said simultaneous presentation.

10. The ECG context controller of claim 9, wherein the ECG context recording subcontroller is installed within one of an ECG monitoring device or an ECG therapy device; and wherein the ECG context diagnostic subcontroller is installed within one or distributed among by the ECG monitoring device, the ECG therapy device, an ECG workstation and an ECG server.

11. The ECG context controller of claim 9, wherein the ECG context recording subcontroller is configured to synchronize the at least one of the recording of the video clip and the recording of the audio clip to a specified time period of the recording of the ECG test.

12. The ECG context controller of claim 11, wherein the ECG context recording subcontroller is configured, in communication with at least one of a video source and an audio source, to control one of:

a video transmission by the video source illustrative of the clinical context of the ECG test during the specified time period of the recording of the ECG test; and an audio transmission by the audio source illustrative of the clinical context of the ECG test during the specified time period of the recording of the ECG test.

13. The ECG context controller of claim 11, wherein the ECG context recording subcontroller is configured, in communication with at least one of a video recorder and an audio recorder, to control one of:

the recording of the video clip by the video recorder during the specified time period of the recording of the ECG test; and the recording of the audio clip by the audio recorder during the specified time period of the recording of the ECG test.

14. The ECG context controller of claim 13, wherein the ECG context diagnostic subcontroller (90) is configured to control one of:

an automatic playing of the video clip in synchronization with an opening of an ECG context window illustrating the recording of the ECG test; and an automatic playing of the audio clip in synchronization with the opening of the ECG context window illustrating the recording of the ECG test.

15. The ECG context controller of claim 13, wherein the ECG context diagnostic subcontroller is configured to control one of:

an automatic playing of the video clip in response to a user interaction with the recording of the ECG test as illustrated in an ECG context window; and an automatic playing of the audio clip in response to the user interaction with the recording of the ECG test as illustrated in the ECG context window.

16. An ECG context testing and diagnostic method, comprising:

controlling, via at least one ECG test controller, a recording of an ECG test;

controlling, via at least one ECG context controller, a synchronization of the recording of the ECG test by the ECG test controller with at least one of a recording of a recording of a video clip illustrative of a clinical context of the ECG test and a recording of an audio clip informative of a clinical context of the ECG test; and controlling, via at least one ECG context controller, a simultaneous presentation of a displaying of the recording of the ECG test with at least one of a playing of the video clip and a playing of the audio clip, wherein the presentation includes an ECG graph display and a toolbar, wherein the ECG context controller is further configured to record a symptom sync marker based on user input during the ECG test, indicative of a timing of a user describing occurrence of a symptomatic event during the ECG test, and wherein the symptom sync marker is further presented during said simultaneous presentation.

17. The ECG context testing and diagnostic method of claim 16, wherein the controlling, via the ECG context controller, of the synchronization of the recording of the ECG test by the ECG test controller with at least one of the recording of the video clip and the recording of the audio clip includes:

synchronizing, via the ECG context controller, the at least one of the recording of the video clip and the recording of the audio clip to a specified time period of the recording of the ECG test.

18. The ECG context testing and diagnostic method of claim 17, wherein the synchronizing, via the ECG context controller, of the at least one of the recording of the video clip and the recording of the audio clip to a specified time period of the recording of the ECG test includes at least one of:

controlling, via the ECG context controller, a video transmission illustrative of the clinical context of the ECG test by a video source during the specified time period of the recording of the ECG test;

controlling, via the ECG context controller, an audio transmission illustrative of the clinical context of the ECG test by the audio source during the specified time period of the recording of the ECG test;

controlling, via the ECG context controller, the recording of the video clip by an video recorder during the specified time period of the recording of the ECG test; and controlling, via the ECG context controller, the recording of the audio clip by an audio recorder during the specified time period of the recording of the ECG test.

19. The ECG context testing and diagnostic method of claim 16, wherein the controlling, via at least one ECG context controller, of the simultaneous presentation of the display of the recording of the ECG test with at least one of the playing of the video clip and the playing of the audio clip includes at least one of:

controlling, via the ECG context controller, an automatic playing of the video clip in synchronization with an opening of an ECG context window illustrating the recording of the ECG test; and controlling, via the ECG context controller, an automatic playing of the audio clip in synchronization with the opening of the ECG context window illustrating the recording of the ECG test.

20. The ECG context testing and diagnostic method of claim 16, wherein the controlling, via at least one ECG context controller, of the simultaneous presentation of the display of the recording of the ECG test with at least one of the playing of the video clip and the playing of the audio clip includes at least one of:

controlling, via the ECG context controller, an automatic playing of the video clip in response to a user interaction with the recording of the ECG test as illustrated in the ECG context window; and controlling, via the ECG context controller, an automatic playing of the audio clip in response to the user interaction with the recording of the ECG test as illustrated in the ECG context window.

* * * * *